United States Patent
Cai et al.

(10) Patent No.: US 11,996,173 B1
(45) Date of Patent: *May 28, 2024

(54) SYSTEM AND METHOD FOR TIMELY MULTI-CHANNEL NOTIFICATION OF TREATMENT

(71) Applicant: IQVIA Inc., Parsippany, NJ (US)

(72) Inventors: Yong Cai, Bala Cynwyd, PA (US); Bob Doyle, Wayne, PA (US); Dong Dai, Dresher, PA (US); Wenzhe Lu, Parsippany, NJ (US); Emily Zhao, Wayne, PA (US); Steven Rosztoczy, Warrington, PA (US)

(73) Assignee: IQVIA Inc., Parsippany, NJ (US)

( * ) Notice: Subject to any disclaimer, the term of this patent is extended or adjusted under 35 U.S.C. 154(b) by 853 days.

This patent is subject to a terminal disclaimer.

(21) Appl. No.: 16/813,213

(22) Filed: Mar. 9, 2020

Related U.S. Application Data

(63) Continuation of application No. 15/136,745, filed on Apr. 22, 2016, now Pat. No. 10,586,614.

(51) Int. Cl.
*G16H 10/60* (2018.01)
*G06N 3/088* (2023.01)
*G16H 50/70* (2018.01)

(52) U.S. Cl.
CPC ............. *G16H 10/60* (2018.01); *G06N 3/088* (2013.01); *G16H 50/70* (2018.01)

(58) Field of Classification Search
CPC ......... G16H 10/60; G16H 50/70; G06N 3/088
See application file for complete search history.

(56) References Cited

U.S. PATENT DOCUMENTS

| | | |
|---|---|---|
| 2007/0067004 A1 | 3/2007 | Boveja et al. |
| 2009/0254392 A1 | 10/2009 | Zander |
| 2009/0287837 A1 | 11/2009 | Felsher |
| 2009/0323918 A1 | 12/2009 | Opaluch et al. |
| 2012/0072583 A1 | 3/2012 | Kupferman et al. |

(Continued)

OTHER PUBLICATIONS

Allenby et al., "Hierarchical Bayes Models: A Practitioners Guide," SSRN 655541, Jan. 2005, 44 pages.

(Continued)

*Primary Examiner* — Jay M. Patel
(74) *Attorney, Agent, or Firm* — Fish & Richardson P.C.

(57) ABSTRACT

A computer-assisted method to timely provide notifications of treatments, the method including receiving de-identified longitudinal medical records, each de-identified longitudinal medical record representing a record of a different anonymized patient and encoding information identifying a treatment received by the anonymized patient and receiving notification data including notification records, each notification record encoding information identifying a channel through which the notification was provided. The method includes determining a first channel impact model representing an impact of a notification provided through a first channel on a treatment being received, a second channel impact model representing an impact of a notification provided through a second channel on a treatment being received, and determining a multi-channel impact model representing an impact of notifications being provided through both the first channel and the second channel on a treatment being received.

20 Claims, 5 Drawing Sheets

(56) References Cited

U.S. PATENT DOCUMENTS

| | | | |
|---|---|---|---|
| 2013/0159021 A1* | 6/2013 | Felsher | G16H 10/60 |
| | | | 705/3 |
| 2014/0052475 A1* | 2/2014 | Madan | G16H 50/30 |
| | | | 705/3 |
| 2014/0081669 A1 | 3/2014 | Raduchel | |
| 2014/0327544 A1* | 11/2014 | Ramsdell | G16H 40/67 |
| | | | 340/573.1 |
| 2014/0357961 A1 | 12/2014 | Meltzer et al. | |
| 2015/0046192 A1* | 2/2015 | Raduchel | H04W 8/18 |
| | | | 705/3 |
| 2015/0134346 A1 | 5/2015 | Hyde et al. | |
| 2015/0244687 A1 | 8/2015 | Perez et al. | |
| 2015/0269355 A1* | 9/2015 | Tidor | G16H 10/20 |
| | | | 705/3 |
| 2015/0348591 A1 | 12/2015 | Kaps et al. | |
| 2017/0161439 A1 | 6/2017 | Raduchel et al. | |

OTHER PUBLICATIONS

Breiman, "Random forests," Machine Learning, Oct. 2001, 45(1):5-32.

Galar et al., "A review on ensembles for the class imbalance problem: bagging-, boosting-, and hybrid-based approaches," IEEE Transactions on Systems, Man, and Cybernetics, Part C (Applications and Reviews), Aug. 8, 2011, 42(4):463-484.

Haario et al., "An adaptive Metropolis algorithm," Bernoulli, 2001, 7(1):223-242.

Hawkes et al., "Spectra of some self-exciting and mutually exciting point processes," Biometrika, Apr. 1971, 58(1):83-90.

He et al., "Learning from imbalanced data," IEEE Transactions on Knowledge and Data Engineering, Jun. 26, 2009, 21(9):1263-1284.

López et al., "An insight into classification with imbalanced data: Empirical results and current trends on using data intrinsic characteristics," Information Sciences, Nov. 20, 2013, 250:113-141.

Vihola, "Robust adaptive Metropolis algorithm with coerced acceptance rate," Statistics and Computing, Aug. 4, 2011, 22(5):997-1008.

Xu et al., "Path to purchase: A mutually exciting point process model for online advertising and conversion," Management Science, Apr. 16, 2014, 60(6):1392-1412.

\* cited by examiner

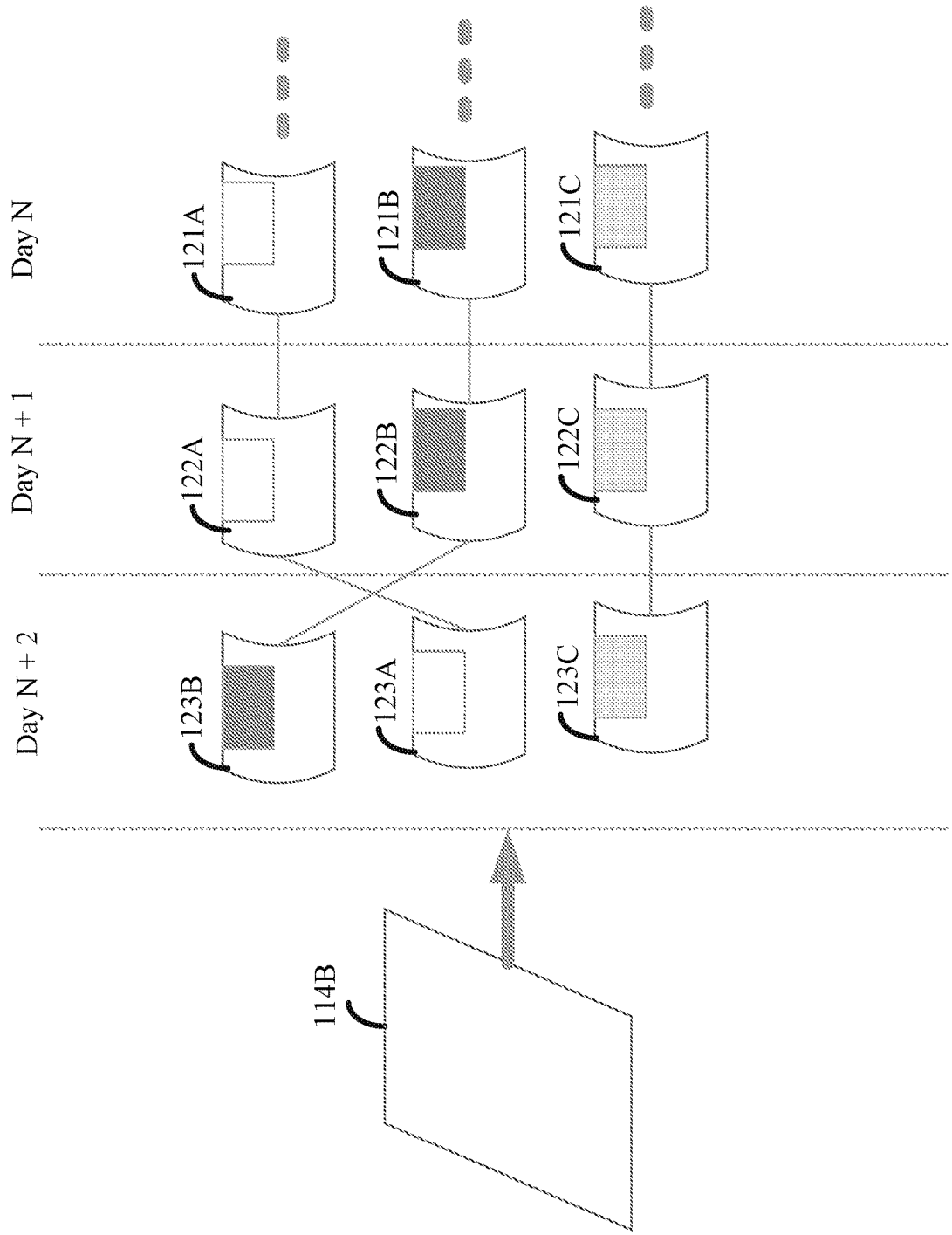

SYSTEM AND METHOD FOR TIMELY MULTI-CHANNEL NOTIFICATION OF TREATMENT

CROSS-REFERENCE TO RELATED APPLICATIONS

This application is a continuation of U.S. application Ser. No. 15/136,745, filed Apr. 22, 2016 now issued U.S. Pat. No. 10,586,614

BACKGROUND

Medical patients may receive various treatments. For example, a medical patient may be prescribed medication by a healthcare professional.

Overview

In one aspect, some implementations provide a computer-implemented method that includes actions of receiving, from one or more database systems each including non-volatile data storage devices, de-identified longitudinal medical records, each de-identified longitudinal medical record representing a record of a different anonymized patient and encoding information identifying a treatment received by the anonymized patient, information identifying a time the treatment was received, and an identifier that uniquely distinguishes the anonymized patient from other anonymized patients, the records devoid of information identifying the patients. Additional actions include receiving, from one or more database systems each including non-volatile data storage devices, notification data including notification records, each notification record encoding information identifying a channel through which the notification was provided, information identifying a time the notification was received, and information referring to a recipient that received the notification and identifying, from the de-identified longitudinal medical records, anonymized patients that received the treatment. Further actions include identifying, from the notification data, notifications for the treatment that were received by the recipients, determining, for each of the identified notifications that were received by the recipients, whether the recipient is an anonymized patient identified as having received the treatment, and obtaining a first set of recipients identified as having received the treatment, having received a notification through the first channel, and not having received a notification through the second channel. Additional actions include determining a first channel impact model representing an impact of a notification provided through the first channel on a treatment being received based on the first set of recipients, obtaining a second set of recipients identified as having received the treatment, having received a notification through the second channel, and not having received a notification through the first channel, determining a second channel impact model representing an impact of a notification provided through the second channel on a treatment being received based on the second set of recipients, obtaining a third set of recipients identified as having received the treatment, having received a notification through the first channel and having received a notification through the second channel, determining a multi-channel impact model representing an impact of notifications being provided through both the first channel and the second channel on a treatment being received based on the third set of recipients, and for each of the recipients that received the treatment and received notifications through both the first channel and the second channel, determining an impact of the notifications being received through both the first channel and second channels on the recipient receiving the treatment based on the first channel impact model, the second channel impact model, and the multi-channel impact model.

Implementations may include one or more of the following features. In certain aspects, the first channel includes a digital channel and the second channel includes a non-digital channel. In some aspects, the first channel impact model represents an impact of a notification through the first channel based on a time relationship between when the first channel notification was received and when the treatment was received. In some implementations, determining a first channel impact model representing an impact of a notification provided through the first channel on a treatment being received based on the first set of recipients includes determining (i) a time decay factor for the first channel that represents an expected decay across time of an impact of a notification through the first channel and (ii) an impact delay parameter for the first channel that represents an expected time delay before a notification through the first channel is expected to impact whether a treatment is received.

In certain aspects, determining a first channel impact model representing an impact of a notification provided through the first channel on a treatment being received based on the first set of recipients includes providing the first set of recipients as training data for a machine-learning neural network to output the first channel impact model. In some aspects, determining, for each of the identified notifications that were received by the recipients, whether the recipient is an anonymized patient identified as having received the treatment includes determining that the information referring to a recipient that received the notification and the identifier that uniquely distinguishes the anonymized patient from other anonymized patients both refer to the same person. In some implementations, determining a multi-channel impact model representing an impact of notifications being provided through both the first channel and the second channel on a treatment being received based on the third set of recipients includes determining the multi-channel impact model based on oversampling from the third set of recipients and undersampling from recipients that are not in the third set of recipients. In some aspects actions include determining a forecast model based on (i) impacts of the notifications through the first channel on the recipients receiving the treatment based on the first channel impact model, (ii) impacts of the notification through the second channel on the recipients receiving the treatment based on the second channel impact model, and (iii) the impacts of the notifications being received through both the first channel and second channels on the recipients receiving the treatment based on the first channel impact model, the second channel impact model, and the multi-channel impact model.

In certain aspects actions include scheduling notifications based on the forecast model. In some implementations, scheduling notifications based on the forecast model includes determining a notification plan for timely notifying potential patients of treatments based on the forecast model. In some aspects determining a notification plan for timely notifying potential patients of treatments based on the forecast model includes receiving notification constraints for the plan, determining that increasing a number of notifications for the first channel increases a number of treatments received according to the forecast model and satisfies the notification constraints, and determining a total number of notifications for the first channel that increases total forecasted number of received treatments.

In certain aspects determining an impact of the notifications being received through both the first channel and second channels on the recipient receiving the treatment based on the first channel impact model, the second channel impact model, and the multi-channel impact model is based on time relationships between when the notifications were received and when the treatment was received. In some aspects determining a multi-channel impact model representing an impact of notifications being provided through both the first channel and the second channel on a treatment being received based on the third set of recipients is based on the first channel impact model and the second channel impact model. In some implementations an anonymized patient includes a patient for which the patient's identity cannot be determined but is distinguishable from other anonymized patients.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 1C illustrates an example of linking medical data of the patients.

Like reference symbols in the various drawings indicate like elements.

DETAILED DESCRIPTION

Figure 1A:
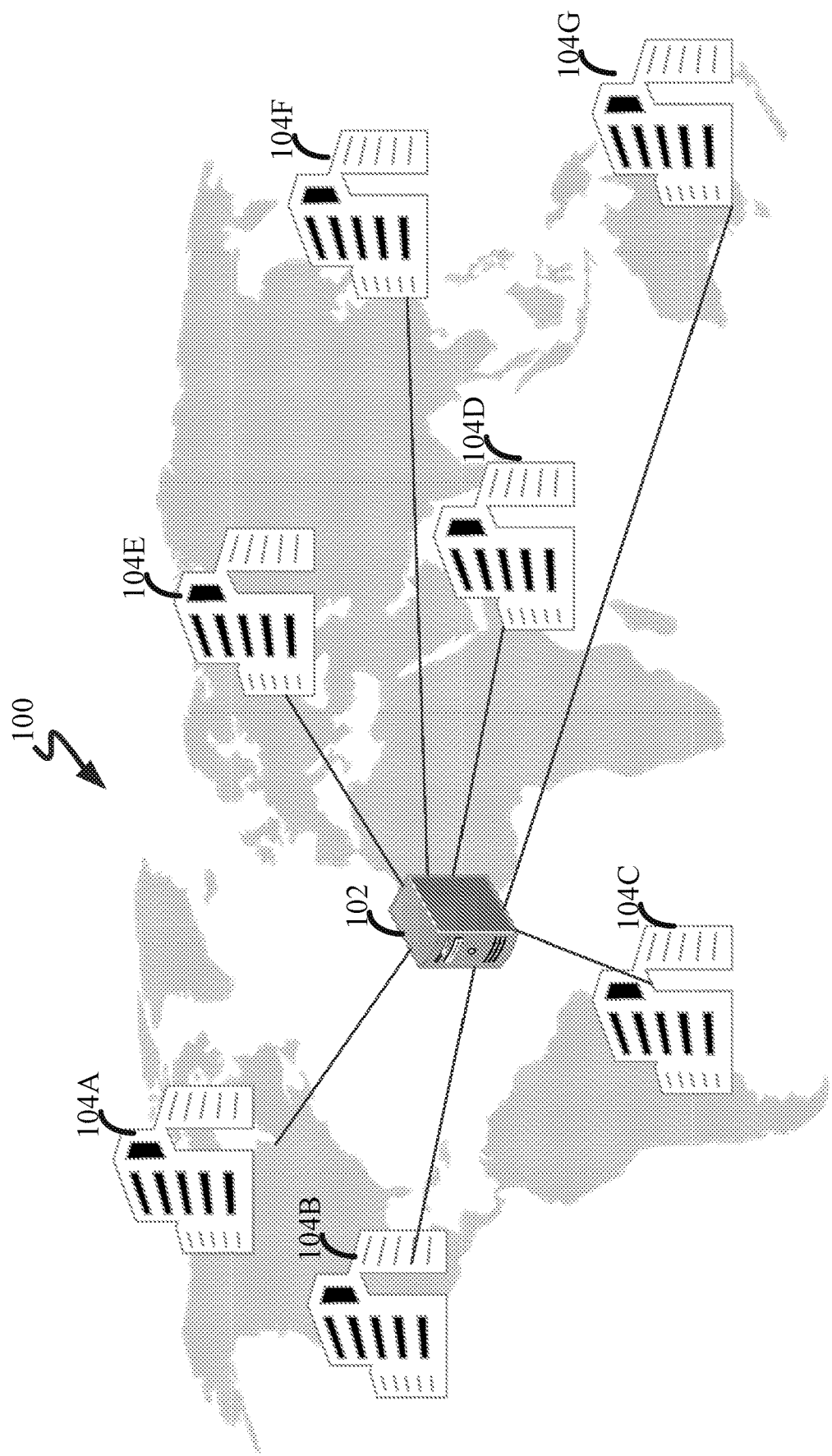
FIG. 1A illustrates an example of a system for deriving de-identified longitudinal medical data from various data supplier sites.

Reconciling disparate records from across different databases can be computationally burdensome to the extent that many desirable database operations are precluded across large and complex databases. For example, in the health care field, a variety of epidemiological studies would reveal links between disparate events. These problems are particularly acute in that the underlying databases may be de-identified in order to satisfy medical privacy concerns. Further, the size of the databases, which can include complex coding for complex and disparate diagnoses may make establishing links between different events even more computationally intensive as a specified item may be compared against countless other items, diagnoses, stimuli, and conditions. These operations are further complicated by different data sources that are formatted in different conventions and with varying degrees of completeness. Further, databases may be constantly updated with large volumes of new information. Thus, newly-received records must be reconciled with and compared to existing records and databases in order to ascertain new trends and real-time information.

The problem is particularly acute where longitudinal data associated with a de-identified label is reconciled between two different data sources with two different time sequences that describe different and sometimes unrelated activity. In order to perform the requisite correlation between the two different data sources, the data must be formatted in a manner that facilitates ready comparison of two different data points from each of the data sources. Once rapid comparison of disparate sources can be relied upon, an organization, such as a Patient Safety Organization (PSO) can act in reliance upon the identified correlations and work to address the correlations and derived identifications. For example, one such correlation may be associated with a breach in the desired activity (e.g., a standard of care). A medical administrator then may work to identify these deviations as fault or alarm conditions and take corrective action in real-time. Note that the deviations need not formally be relative to some regulatory standard (e.g., the standard of care). Instead, the deviation may exist relative to desired behavior (e.g., an internal hospital policy).

Based on the architecture and organization described above, a variety of configurations may be used to facilitate analysis of patent records organized longitudinally according to a first timeline relative to another source of data organized according to a second timeline. In one configuration, this disclosure generally describes a system and a method for timely providing notifications of treatments to a patient population, and the reaction to notifications. There may be significant problems in determining an impact of a notification about a treatment provided to a patient on a receipt of the treatment by the patient as, in healthcare, treatments generally do not immediately follow notifications of treatments. For example, a patient may not get a prescription without a doctor, the doctor may recommend other lifestyle changes, other treatments, order tests, etc. before prescribing the patient a drug, the patient then may need to go to the pharmacy to get the prescribed drug. Additionally, the patient may need to have insurance or some other way to supplement the expense of the prescribed drug before making the purchase. Additionally, in healthcare, patient information generally must be anonymized. As described in this description, treatment may refer to medical events such as seeing a doctor, receiving a prescription, receiving prescribed drugs from a pharmacy or undergoing an operation.

Accordingly, in some implementations, de-identified longitudinal medical records may be collected from data servers at medical service providers that record filled prescription information, medical operations, doctor visits, or other medical events for patients. The information may generally include records of different anonymized patients, where each record identifies one or more treatments received by the anonymized patient, the one or more times the treatments were received by the anonymized patient, and an identifier that uniquely distinguishes the anonymized patient from other anonymized patients. The identifier may refer to a de-identified patient, which may also be referred to as an anonymized patient. The de-identification means no identity information, such as name, address, birth date, or social security information, is available in the recorded information. Instead, each patient is referenced by an anonymous tag that is specific to the patient. Accordingly, an anonymized patient may be a patient for which the patient's identity cannot be determined but is distinguishable from other anonymized patients. Generally, the anonymous tag is doubly encrypted using a key specific to a data supplier (such as a data server at a pharmacy) and another key specific to a longitudinal database.

Additionally, notification data may be collected from data servers of notification providers that record notifications provided to recipients. A notification may include text, one or more images, one or more videos, or one or more audio identifying a treatment. The notifications may be placed in various locations, e.g., on websites, television advertisements, in mobile applications, or radio broadcasts. For example, a first type of notification may be provided through a digital channel, e.g., through a web site or the Internet, and a second type of notification may be provided through a non-digital channel, e.g., television or radio. Different types of notifications may also be provided through a channel. For example, a first type of notification may be provided with an image on a website and a second type of notification may be provided with text on the web site.

The notification data may include notification records that each identify a type of notification provided, a time the notification was received, and the recipient of the notification. Interestingly, relationships between the patients of the medical data and recipients of the notification data may be identified and time relationships between when patients received a treatment and when the patients received a notification regarding the treatment may be determined. The time relationships may then be used to determine impacts of the notifications on the patients receiving the treatment. The impacts of the notifications may be used to forecast a future effect of various types of notification, and a plan for providing notifications in the feature may be determined based on the forecast.

FIG. 1A illustrates an example system 100 for obtaining de-identified longitudinal medical records. The medical records may include treatment data in the form of prescription data. The prescription may include a pharmaceutical product such as a prescription drug approved by a regulatory agency, such as the Federal Drug Administration (FDA), the European Medicines Agency (EMA), the Medicines and Healthcare products Regulatory Agency (MHRA). The pharmaceutical product can also include approved medical devices. The prescriptions may be filled at multiple sites, such as pharmacies 104A to 104G. These sites can cover a geographic region, for example, a region in a particular country. These sites may also be located globally, for example, the North American continent, or the European Union.

Prescription data for each participant patient may be collected from each pharmacy store. In one example, a pharmacy database may collect prescription data from all pharmacy stores on a daily basis. The pharmacy database includes non-volatile data storage devices. Each pharmacy store may house its own data server in communication with the pharmacy database to transfer prescription data on a daily basis. The prescription data records the information about a particular prescription when the prescription was filled. As disclosed herein, the prescription data for each participant patient, as recorded at the pharmacy store at the time of filling, is de-identified such that the data does not include information capable of identifying the particular participant patient. Examples of such identifying information include: patient's name, patient's insurance identification number, patient's Medicare/Medicaid identification number, patient's social security number, patient driver's license number, etc. In some implementations, such identifying information may be converted by a one-way hash-function to generate an alpha-numerical string. The alpha-numerical string conceals the identity of the individual participant patient, thereby maintaining confidentiality of the data as the data is being reported, for example, daily from the sites 104A to 104G to the central server 102. There, data corresponding to the same participant patient may be linked by virtue of the matching alpha-numerical string. Thus, data for the same participant patient may be longitudinally tracked for each individual, without compromising confidentiality of the individual patients, even though the patient can fill the prescription at various stores and the patient can receive a prescription for a healthcare product from various healthcare professionals.

Additionally or alternatively, the de-identified longitudinal medical records may include other forms of data. For example, the de-identified longitudinal medical records may include data describing operations performed on a patient and when the operations were performed, when a patient made a visit to a particular doctor, when a doctor performed a diagnosis on a patient, and other events. In these instances, the sites may be medical service providers that include pharmacy stores and other types of medical service providers, e.g., doctor's offices or hospitals.

Figure 1B:
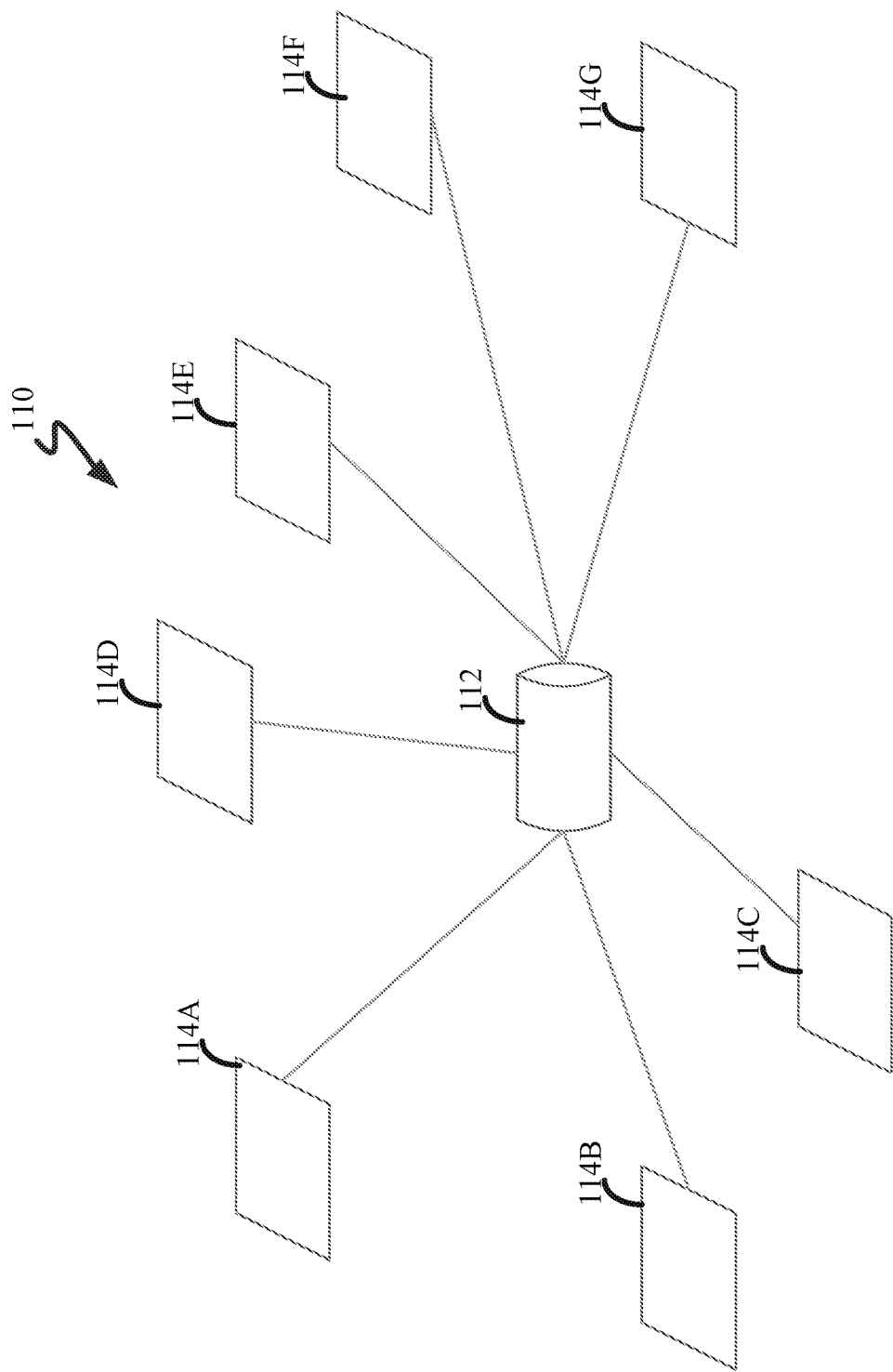
FIG. 1B illustrates an example of a system for aggregating medical data from data servers at medical service providers longitudinally tracking the treatment pattern of human patients.

FIG. 1B illustrates an example work flow 110 for collecting data of patient recipients from data servers at various medical service providers and longitudinally tracking the medical record of each individual patient recipient over time. Data 114A-114G may correspond to prescription data reported from each pharmacy store. In some implementations, data 114-114G may be reported from data servers at each pharmacy store on a daily basis, for example, at the end of business data local time. Data 114A-114G remain de-identified to preserve confidentiality, as disclosed herein. In this illustrated work flow, each pharmacy store may employ the same one-way hashing function to anonymize data records of each patient. As a result, reported prescription data 114A-114G, as received at central server 102 to update database 112, include the same de-anonymized key for prescription records from the same patient, even if the patient may move to another pharmacy store, another healthcare professional, or another healthcare provider (e.g., health insurance carrier, pharmacy insurance carrier). The central server 102 may match prescription data records from the same patient recipient to update database 112, which contains data records reported earlier for the same patient recipient.

In some implementations, however, the de-identified data may be further encrypted before the data is reported to central server 102 to update database 112. For illustration, data 114A-114G may be encrypted using a symmetric encryption key specific to each pharmacy store. The symmetric encryption key may only be known to the pharmacy store and central server 102. Thus, only the participant site can encrypt the de-identified data with the symmetric key and only the central server 102 can decrypt the encrypted de-identified data with the particular symmetric key. In another illustration, a public-key infrastructure (PKI) may be used such that the reported data may be encrypted with the public key of the central server 102 so that only the central server 102 can decrypt using its private key. In other illustrations, the central server 102 and pharmacies 104A-104G may exchange messages using the PKI to establish an agreed-on symmetric key.

As discussed above, the data 114A-114G may correspond to other data besides prescription data. For example, the data 114A-114G may describe operations performed on a patient and when the operations were performed, when a patient made a visit to a particular doctor, when a doctor performed a diagnosis on a patient, and other events received from medical service providers that include pharmacy stores and other types of medical service providers, e.g., doctor's offices or hospitals.

FIG. 1C illustrates an example linkage of daily reported medical data for the patient recipients based on matching anonymized tags. As illustrated, the daily received prescription data (for example, data 114B from pharmacy 104B) correspond to patient recipients. The de-identification process allows such prescription data to remain anonymous. In some implementations, the de-identified data from the same patient may be linked at central server 102. As illustrated, data are received on different days for the patient recipients. For example, on time point N, de-identified prescription data 121A to 121C may be received. Likewise, on time point N+1, de-identified prescription data 122A to 122C are received. Similarly, on time point N+2, de-identified data 123A to 123C may be received. These de-identified prescription data correspond to different patient recipients. Based on matching tags, such as matching de-identified alpha-numerical strings, the de-identified prescription data from each patient recipient may be linked and hence the prescription activity of a particular patient recipient can be longitudinally tracked. In some implementations, the matching tags may include graphic representations as well as alpha-numerical strings. The graphic representations are also de-identified to remove personally identifiable information of the participant patient. In some instances, the alpha-numerical strings or graphical representations may be tags to the actual prescription data record, which may be referred to as part of the metadata. In other instances, the alpha-numerical strings or graphical representations may be embedded to the actual prescription data record itself. In still other instances, the alpha-numerical strings or graphical representations may be part of the metadata and embedded in the actual prescription data record. The implementations of both the tag and the embedding may further deter alterations or modifications of the data records being reported from each participant site. When the received daily data records are linked with earlier data records of the same patient recipients, database 112 may be updated. The updated database may allow a variety of data analytics to be generated, revealing the interesting insights of prescription usage pattern for each patient recipient as well as the statistical prescription pattern of each healthcare professional, as discussed below.

As discussed above, the de-identified prescription data 121A to 121C may correspond to other de-identified data besides prescription data. For example, the de-identified data may describe operations performed on a patient and when the operations were performed, when a patient made a visit to a particular doctor, when a doctor performed a diagnosis on a patient, and other events.

Figure 2:
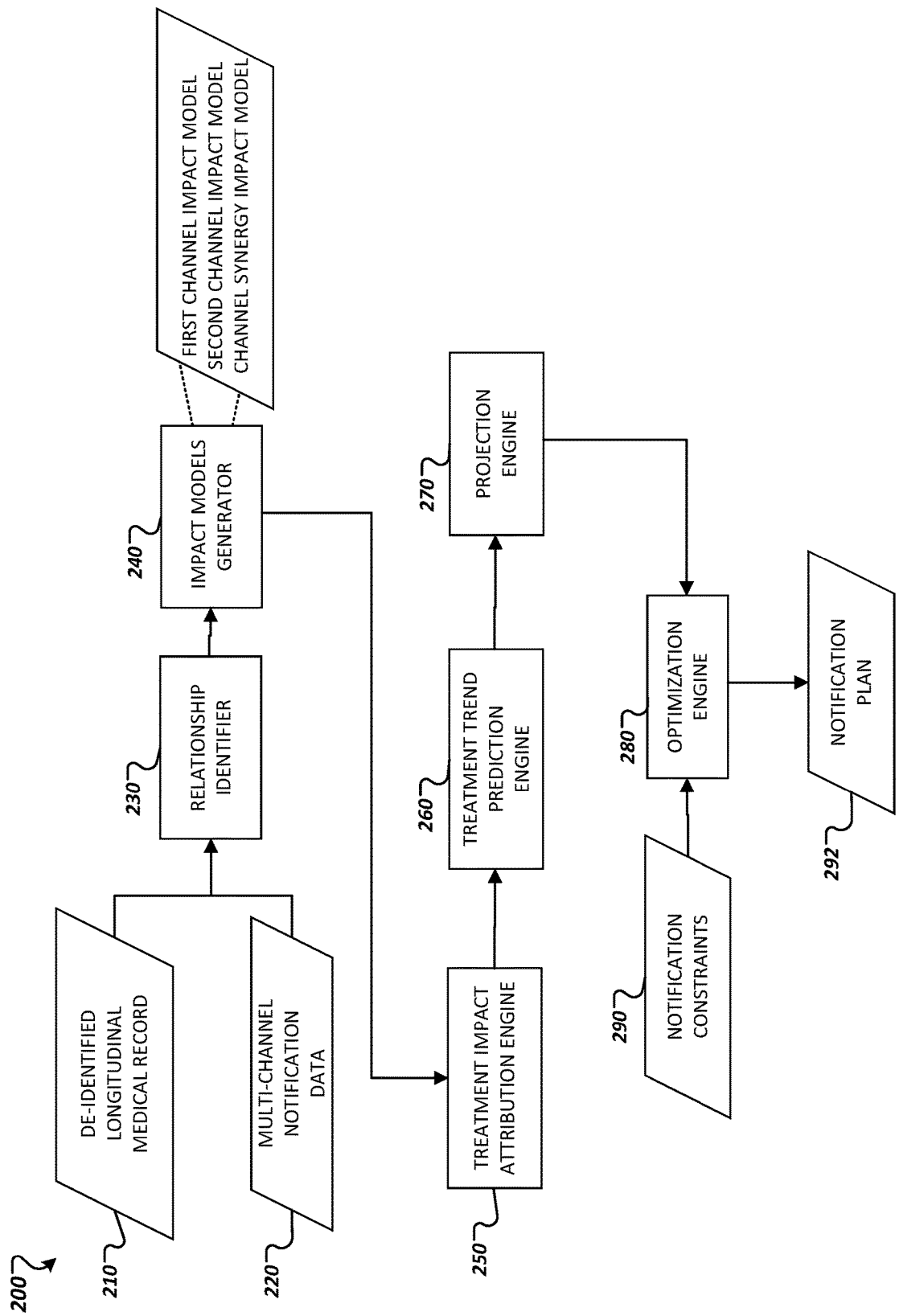
FIG. 2 illustrates an example of a block diagram of a system for providing timely multi-channel notification of treatments.

FIG. 2 illustrates an example of a block diagram of a system 200 for providing timely multi-channel notification of treatments. The system 200 may include a relationship identifier 230 that identifies relationships between de-identified longitudinal medical records and notification data, an impact models generator 240 that determines impact models for each channel and synergy between the channels based on the relationships, a treatment impact attribution engine 250 that determines an impact of notifications on a treatment being received, a treatment trend prediction engine 260 that determines an initial forecast for the anonymized patients based on the determined impacts, a projection engine 270 that determines a projected forecast for potential patients from the initial forecast, and an optimization engine 280 that determines a notification plan based on the projected forecast.

In more detail, the relationship identifier 230 may identify relationships between patients anonymously identified by the de-identified longitudinal medical records 210 and recipients of identified by the notification data 220. As described above, the de-identified longitudinal medical records 210 may be collected from data servers at medical service providers that record filled prescription information, medical operations, doctor visits, or other medical events for patients. The information may generally include records of different anonymized patients, where each record identifies one or more treatments received by the anonymized patient, the one or more times the treatments were received by the anonymized patient, and an identifier that uniquely distinguishes the anonymized patient from other anonymized patients. The notification data 220 may be collected from data servers of notification providers that record notifications provided to recipients. The notification data may include notification records that each identify a type of notification provided, a time the notification was received, and the recipient of the notification. As described above, the type of notification may include an indication of one or more of a channel for the notification, a subchannel for the notification, and the notification itself. For example, the indication may indicate that an image-based notification was provided through a non-digital television channel and a particular subchannel of "Channel 5" and a text-based notification was provided through a digital online channel and a particular subchannel of "Health.com."

The relationship identifier 230 may obtain the de-identified longitudinal medical records 210 and the notification data 220, and identify relationships between anonymized patients and recipients based on identifying, from the de-identified longitudinal medical records, anonymized patients that received the treatment, identifying, from the notification data, notifications for the treatment that were received by the recipients, and determining, for each of the identified notifications that were received by the recipients, whether the recipient is an anonymized patient identified as having received the treatment. For example, the relationship identifier 230 may identify from a medical record that an anonymized patient identified as "ad978zfvd3426oiu90" received a particular treatment, identify from the notification data that a recipient identified as "ad978zfvd3426oiu90" received a notification for the particular treatment, and that the identifiers both have the value "ad978zfvd3426oiu90." In some implementations, the relationship identifier 230 may, one or more of, determine whether notification records are for notifications for other treatments and determine to ignore those notifications or determine whether treatments indicated by the medical records are for other treatments and determine to ignore those indications in the medical records. Additionally or alternatively, the relationship identifier 230 may determine that the identifiers match. For example, the relationship identifier 230 may determine that the identifier of an anonymized patient in a medical record indicates demographics of the anonymized patient, that are insufficiently detailed to identify the anonymized patient, match demographics indicated by the identifier of a recipient in a notification record.

The impact models generator 240 may determine impact models based on the relationships determined by the relationship identifier 230. The impact models generator 240 may generate an impact model for each channel that notifications are provided through, and one or more additional impact models that represent synergy of providing notifications through multiple channels. For example, the impact models generator 240 may generate a first impact model for digital notifications, a second impact model for non-digital notifications, and a third impact model for synergy from both digital and non-digital notifications. The synergy of providing notifications through multiple channels may represent an impact that a recipient may receive a treatment over the aggregation of the impacts of each individual channel. For example, recipients of a non-digital notification for a treatment may have a 10% chance of getting the treatment and recipients of a digital notification for a treatment may have a 5% chance of getting the treatment, but recipients of both digital and non-digital notifications may have a 30% chance of getting the treatment.

Each of the channel specific impact models may represent an impact of a notification on a treatment being received based on a time relationship between when a treatment was received by a patient and a notification was received by a recipient corresponding to the patient. For example, the impact models generator 240 may determine an impact model that models an impact of 66% for a notification received fifteen days before a treatment is received and an impact of 33% for a notification received thirty days before a treatment is received. In some implementations, the impact model may include a model that is exponentially decayed from time when the notification was initially provided to a patient to a time the treatment was received by the patient. For example, the impact models generator 240 may determine coefficients for an exponential function that receives as an input a time relationship and outputs an impact.

In some implementations, the channel specific impact models may include both a time decay parameter and an impact delay parameter. The time decay parameter may represent a decay of an impact across time and the impact delay parameter may represent a duration after which notifications may be considered to impact a recipient receiving a treatment. For example, a time decay parameter may indicate that every day an impact of a notification is reduced by 25% and an impact delay parameter may indicate that a non-digital channel notification won't result in a recipient receiving a treatment until at least three days later the notification is received. Accordingly, in the example, any non-digital channel notification that was received less than three days before the recipient received the treatment will not be considered to have impacted the recipient having received the treatment, and decay of the impact of the non-digital channel will not begin to decay according to the time decay parameter until three days after the recipient received the non-digital notification.

In some implementations, each of the channel specific impact models may represent an impact of notifications provided through multiple sub-channels within a channel. For example, the digital impact model may represent an impact of notifications provided through multiple websites and the non-digital impact model may represent an impact of notifications provided through multiple conventional television channels.

The impact models generator 240 may determine the single channel impact models based on determining time relationships between times when treatments were received by anonymized patients and times when notifications were received by recipients corresponding to the anonymized patients, determining associations between one or more time relationships for notifications received by the anonymized patients, and determining the impact model from the determined associations between the time relationships. For example, the impact models generator 240 may determine from the medical records 210 that anonymized patient "ad978zfvd3426oiu90" fulfilled a prescription for "Drug X" on Jul. 23, 2015, from the notification data 220 that a recipient determined to correspond to anonymized patient "ad978zfvd3426oiu90" received a notification regarding "Drug X" on Jul. 8, 2015, and as result, determine a time relationship of fifteen days, determine from the notification data 220 that a recipient determined to correspond to anonymized patient "ad978zfvd3426oiu90" received a notification regarding "Drug X" on Jun. 23, 2015, and as result, determine a time relationship of thirty days, determine that both notifications were received by anonymized patient "ad978zfvd3426oiu90," and in response, determine that the time relationship of thirty days and fifteen days for anonymized patient "ad978zfvd3426oiu90" are both associated with anonymized patient "ad978zfvd3426oiu90" receiving the treatment. In another example, the impact models generator 240 may determine from the medical records 210 that anonymized patient "oinj32o908twvc2" fulfilled a prescription for "Drug X" on Jul. 1, 2015 and from the notification data 220 and determined relationships that a recipient corresponding to anonymized patient "oinj32o908twvc2" received a notification regarding "Drug X" on Jun. 1, 2015, and as result, determine a time relationship of thirty days.

From the associations between time relationships, the impact models generator 240 may determine the impact model. For example, the impact models generator 240 may use machine-learning, e.g., Least Absolute Shrinkage and Selection Operator (LASSO), Cox Proportional Hazard (CPH) model, ensemble learning by random survival forest (RSF), with the de-identified longitudinal medical records 210, the notification data 220, and the determined time relationships to determine coefficients of an exponential function that includes both a time decay parameter and an impact delay parameter. The impact models generator 240 may use random survival forest by randomly under sampling patients indicated by the medical records 210 that were not treated with the particular treatment, combine the under sampled data with the data of anonymized patients indicated by the medical records 210 that were treated with the particular treatment, apply random survival forest to derive an impact of a notification each day to the treatment being received, e.g., scores of impact of a notification each day to treatment being received may be generated, repeating these steps, e.g., for 50,000, 100,000 or some other number of times, and average the impacts, and then fitting a curve to impact decay over time based on the averaged impacts.

For example, the impact models generator 240 may determine that (i) recipients that received a television notification were no more likely to receive a treatment within three days of receiving the television notification than individuals that did not receive the television notification and (ii) that those that received the television notification were more likely to receive the treatment after three days of receiving the television notification than those that did not receive the television notification, and in response, determine the impact delay parameter for the television notification is three days and then use the impact delay parameter to calculate the time decay parameter based on a reduction in impact of the television notification for each day after receipt where the reduction begins three days after the television notification is received.

In generating impact models for notifications across multiple channels, the impact models generator 240 may generate the impact model for each of the channels and then use the impact model for each of the channels to generate a synergy impact model. For example, to generate the impact models for notifications provided through digital and non-digital notifications, the impact models generator 240 may obtain a first sample of recipients that only received digital notifications, a second sample of recipients that only received non-digital notifications, and a third sample of recipients that received both digital and non-digital notifications. The various samples may over sample from recipients that received the treatment and under sample from recipients that did not receive the treatment. For example, the impact models generator 240 may identify all recipients of a television notification that received a treatment and did not receive an online notification and generate a first sample of recipients that only received the television notification by including all the identified recipients and including 5%, 10%, or 20%, or some other amount of additional recipients of the television notification that did not receive the treatment, and perform a similar process to generate the second sample and third sample.

The impact models generator 240 may then use machine-learning on the first sample to obtain the digital channel specific impact model, use machine-learning on the second sample to obtain the non-digital channel specific impact model, and then use machine-learning on the third sample in combination with the digital channel specific impact model and the non-digital channel specific impact model to generate the synergy impact model. For example, the impact models generator 240 may use machine-learning to determine a time decay parameter and an impact delay parameter for the digital channel specific impact model that best matches the first sample.

The treatment impact attribution engine 250 may determine an impact of notifications on a treatment being received based on the impact models determined by the impact models generator 240. In particular, the treatment impact attribution engine 250 may attribute an impact of different types of notifications indicated by the notification data 220 and an impact of synergy of different types of notifications over all anonymized patients identified by the medical records 210 and time based on the impact models. For example, for a treatment that was received by a recipient of two digital channel notifications and no non-digital channel notifications, the treatment impact attribution engine 250 may determine the impact of each digital channel notification according to a digital channel impact model. In another example, for a treatment that was received by a recipient of a digital channel notification and a non-digital channel notification, the treatment impact attribution engine 250 may determine the impact of the digital channel notification according to the digital channel impact model, determine the impact of the non-digital channel notification according to the non-digital channel impact model, and determine the impact of synergy between the channels according to the multi-channel impact model.

For each type of notification, the treatment impact attribution engine 250 may sum an impact of the type of notification on each anonymized patient, indicated by the medical records 210 as having received the treatment, based on the impact model for the notification. From the attribution, the treatment impact attribution engine 250 may determine different impacts of different types of notifications and a synergy of different types of notifications. For example, the treatment impact attribution engine 250 may determine that a particular type of notification has twice as much impact as another type of notification, i.e., results in twice as many patients receiving a treatment, and two types of notifications have synergy, e.g., results in more patients receive a treatment than if each person only received a notification of one type.

The treatment trend prediction engine 260 may determine an initial forecast model based on the impacts determined by the treatment impact attribution engine. For example, the treatment trend prediction engine 260 may determine an initial forecast model that models a number of patients identified in the medical records 210 that would receive a treatment based on a number of each type of notification provided and the impact models. A forecast model may store, for each type of notification, a notification type label that is indicative of a relationship between a number of patients receiving a treatment and a number of recipients receiving notifications for the treatment. For example, a first notification type label for a first type of notification may reflect how a number of patients estimated to receive a treatment increases as a number of recipients of a notification of the first type of notification for that treatment increases and a second notification type label for a second type of notification may reflect how a number of patients estimated to receive a treatment increases as a number of recipients of a notification of the second type of notification for that treatment increases.

The treatment trend prediction engine 260 may determine the initial forecast model based on fitting the model to the number of treatments received indicated by the medical records 210 and the notifications provided indicated by the notification data 220. For example, the treatment trend prediction engine 260 may determine an initial forecast model that scales an impact of notifications of all types by an amount so that a number of patients forecasted to receive a treatment best matches the number of patients that actually received the treatment as indicated by the medical records 210 and the notification records 220. The treatment trend prediction engine 260 may determine the initial forecast model as a sigmoid function considering the diminishing effect of number of notifications received by recipients on number of patients that receive a treatment.

The treatment trend prediction engine 260 may generate more accurate initial forecast models as the amount of data increases across time. For example, at nine weeks data up to 100,000 notifications may be available, at thirteen weeks, data up to 150,000 notifications may be available, and at eighteen weeks data up to 200,000 notifications may be available, and the treatment trend prediction engine 260 may fit the initial forecast model to match the data.

The projection engine 270 may determine a projected forecast for potential patients from the initial forecast determined by the treatment trend prediction engine 260. For example, the projection engine 270 may project an initial forecast determined from a subset of patients with indicated by the medical records 210 to a set of all patients indicated by the medical records 210, then project from the set of all patients indicated by the medical records 210 to all recipients of notifications indicated by the notification data 220, and then project from all recipients of the notifications indicated by the notification data 220 to all potential recipients of the notification. The subset of patients of the initial forecast may be patients that have prescription drug activity within a predetermined number of months, e.g., the last three, six, twelve, or another number of months.

The projection engine 270 may project forecasts from a first group to a second group based on scaling on characteristics of the groups. For example, the projection engine 270 may determine that the initial forecast is prepared for a set of one hundred patients where 40% have high blood pressure, and that the medical records 210 for all one thousand patients have 20% with high blood pressure, and in response, modify the initial forecast by a factor of five.

The optimization engine 280 may determine a notification plan based on the projected forecast. For example, the optimization engine 280 may determine to provide one million of a particular type of notification and two million of another type of notification to increase a forecasted number of treatments. The optimization engine 280 may determine the notification plan based on notification constraints 290. The notification constraints 290 may include specifications of one or more of a budget, notification types available, notifications provided so far, notifications allocated, a minimum number of notifications for each type, a maximum number of notifications of each type, a remaining number of notifications to provide for each type, a cost for each type of notification, an available budget for each type of notification, or a total budget for a type of notification. For example, the notification constraints 290 may specify that a total of one million is available for notifications, three types of notifications are available, a first type of notification costs fourteen dollars per million provided, a second type of notification costs eighteen dollars per million provided, and a third type of notification costs sixteen dollars per million provided, and in response, based on the projected forecast model, the optimization engine 280 may determine to allocate two hundred thousand dollars to the first type of notification, five hundred thousand dollars to the second type of notification, and three hundred thousand dollars to the third type of notification.

The optimization engine 280 may receive the notification constraints from a user. For example, the optimization engine 280 may provide a graphical user interface for a user to input the notification constraints and change the notification constraints, and in response may update the notification plan and display the updated notification plan to the user through the graphical user interface.

In some implementations, the optimization engine 280 may receive indications of events and in response update a notification plan. For example, the optimization engine 280 may receive an indication that a flu epidemic is spreading, and in response, may determine to increase a number of allocations of a particular type of notification and decrease a number of allocations of another type of notification.

The optimization engine 280 may then schedule the notifications based on the forecast model. For example, the optimization engine 280 may cause the system 100 to provide notifications to recipients based on the notification plan. In another example, the optimization engine 280 may provide the notification plan to a notification provider for the notification provider to provide notifications in accordance with the notification plan.

Figure 3:
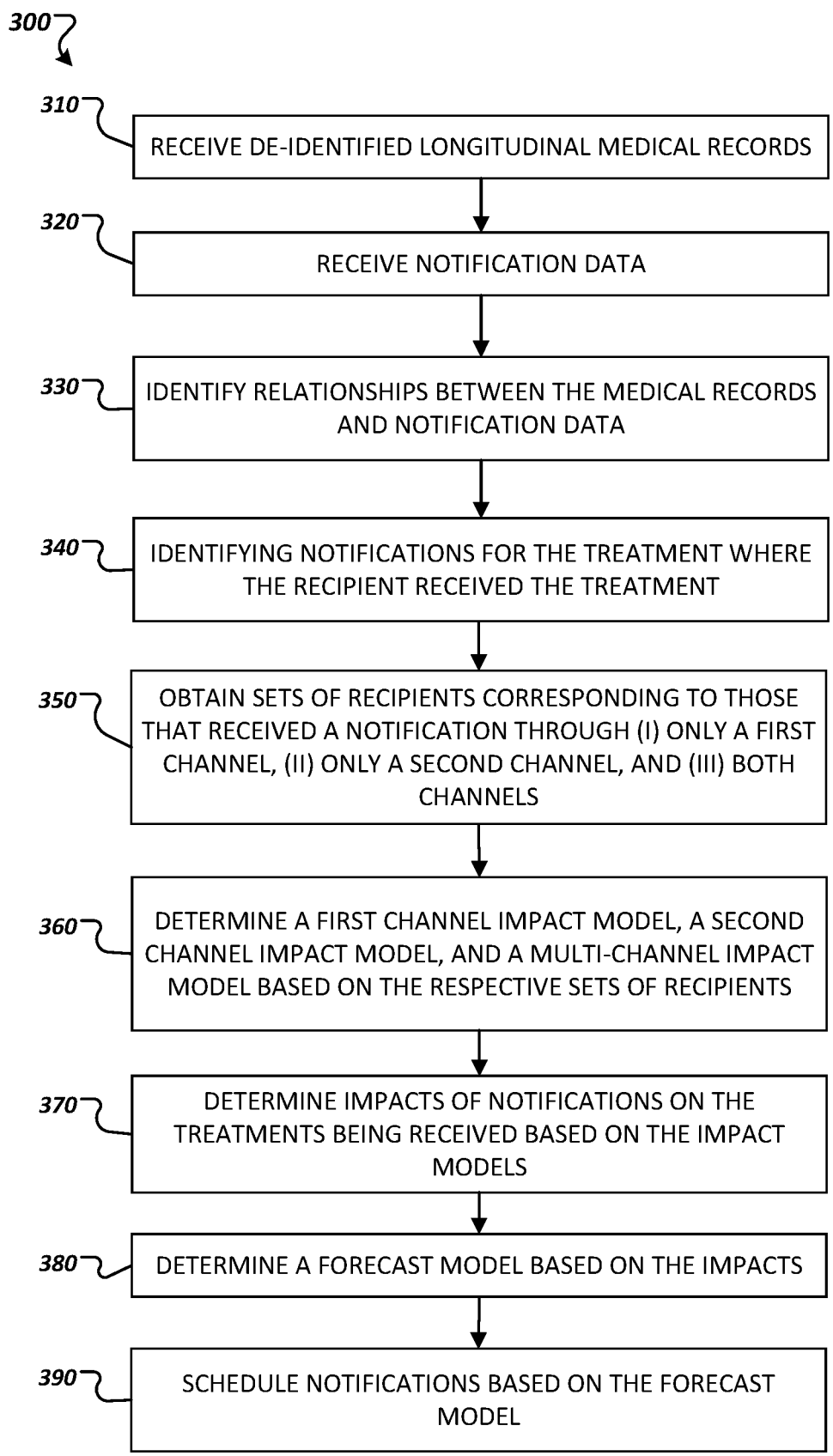
FIG. 3 illustrates an example of a flow chart for providing timely multi-channel notifications of treatments.

FIG. 3 illustrates an example of a flow chart 300 for providing timely multi-channel notifications of treatments. Initially, de-identified longitudinal medical records are received (310). For example, the relationship identifier 230 may receive de-identified longitudinal medical records from a database of a medical server provider. Before, after, or in parallel, notification data is received (320). For example, the relationship identifier 230 may receive notification data from a database of a notification provider.

Thereafter, relationships between the medical records and the notification data may be identified (330). For example, the relationships identifier 230 may determine that a particular medical record indicates that an anonymized patient received a particular treatment, determine that a particular notification record indicates that a recipient received a notification for the particular treatment, and determine that the particular medical record has an identifier, that refers to an anonymized patient, that is the same identifier representing a recipient that is associated with the particular notification record. Thereafter, time relationships between when treatments were received and notification were received may be determined (340). For example, the impact models generator 240 may determine that sixty days passed between when a recipient received a notification of a treatment and an anonymized patient corresponding to the recipient received the treatment.

Next, sets of recipient corresponding to (i) recipients of only notifications through the first channel, (ii) recipients of only notifications through the second channel, and (iii) recipients of notifications through both the first and second channels may be obtained (350). For example, the impact models generator 240 may identify recipients of notifications through the first channel that did not receive notifications through the second channel, identify recipients of notifications through the second channel that did not receive notifications through the first channel, and identify recipients of notifications through both the first channel and the second channel. The impacts model generator 240 may obtain the sets of recipients by oversampling from recipients of corresponding notifications that received a treatment and undersampling from recipients of corresponding notifications that did not receive a treatment.

A first channel impact model, a second channel impact model, and a multi-channel impact model may be determined based on the impact models (360). For example, the impact models generator 240 may determine a first channel impact model based on the set of recipients of notifications through the first channel that did not receive notifications through the second channel, determine the second channel impact model based on the set of recipients of notifications through the second channel that did not receive notifications through the first channel, and determine the multi-channel impact model based on the first channel impact model, second channel impact model, and the set of recipients of notifications through both the first channel and the second channel.

Impacts of notifications on treatments being received may be determined based on the impact models (370). For example, for each time a treatment was received, the treatment impact attribution engine 250 may use the impact models to determine an impact of each notification and a synergy of the notifications on the treatment being received.

Thereafter, a forecast model may be determined based on the impacts (380). For example, the treatment trend prediction engine 260 may determine an initial forecast model for a set of patients based on the impacts and the projection engine 270 may project the initial forecast model to all potential notification recipients. Next, a plan for timely notifying may be determined based on the forecast model (390). For example, the optimization engine 280 may receive the forecast model and notification constraints specified by a user indicating types of notifications available and constraints on providing the notifications, and in response, determine a notification plan indicating how many of each type of notification should be provided.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method comprising:
identifying, from a set of recipients, a first subset of recipients that (i) received a notification through a first channel, (ii) have not received the notification through a second channel, and (iii) have received a treatment, wherein the identifying is based on (i) de-identified medical records indicating treatments received by a set of anonymized patients and (ii) notification records indicating channels through which notifications were provided to the first subset of recipients and a first set of time points when the notifications were received by the first subset of recipients stored in one or more database systems;
identifying, from the set of recipients, a second subset of recipients that (i) have received the notification through the second channel, (ii) have not received the notification through the first channel, and (iii) have received the treatment, wherein the identifying is based on (i) the de-identified medical records indicating treatments received by the set of anonymized patients and (ii) the notification records indicating channels through which notifications were provided to the second subset of recipients and a second set of time points when the notifications were received by the second subset of recipients stored in the one or more database systems;
generating a multi-channel impact model based on a time relationship between when the treatment was received by each patient of the set of anonymized patients and when a notification was received by each recipient of the first subset of recipients and the second subset of recipients, wherein the multi-channel impact model represents an impact of notifications being provided through the first channel and the second channel on a likelihood of one or more recipients in the set of recipients receiving the treatment;
generating a notification plan for timely notifying potential patients of treatments based on the impact represented by the multi-channel impact model, wherein the notification plan indicates one or more notifications to be provided through a corresponding channel to increase a number of treatments to be subsequently received; and
sending the one or more notifications through the first channel or the second channel to respective recipients associated with potential patients based on the notification plan.

2. The method of claim 1, wherein the first channel comprises a digital channel and the second channel comprises a non-digital channel.

3. The method of claim 1, further comprising:
generating a first channel impact model based on the first subset of recipients, wherein the first channel impact model represents a first impact of the notification received through the first channel and treatments received by the first subset of recipients; and
generating a second channel impact model based on the second subset of recipients, wherein the second channel impact model represents a second impact of the notification received through the second channel and treatments received by the second subset of recipients.

4. The method of claim 3, wherein the multi-channel impact model is generated based on the first impact represented by the first channel impact model and the second impact represented by the second channel impact model.

5. The method of claim 3, wherein generating the first channel impact model comprises:
determining a time decay factor associated with the first impact represented by the first channel impact model; and
determining, based on the time decay factor, an expected time delay before the notification received through the first channel is expected to impact whether treatments are received by the first subset of recipients.

6. The method of claim 1, wherein each recipient included in the first subset of recipients and the second subset of recipients is associated with a unique identifier that distinguishes a recipient from other recipients.

7. The method of claim 1, wherein the multi-channel impact model is generated based on:
oversampling data associated with the first subset of recipients and the second subset of recipients; and
undersampling data associated with other recipients not included in either the first subset of recipients and the second subset of recipients.

8. A system comprising:
one or more processors; and
one or more storing devices storing instructions that cause the one or more processors to perform operations comprising:
identifying, from a set of recipients, a first subset of recipients that (i) received a notification through a first channel, (ii) have not received the notification through a second channel, and (iii) have received a treatment, wherein the identifying is based on (i) de-identified medical records indicating treatments received by a set of anonymized patients and (ii) notification records indicating channels through which notifications were provided to the first subset of recipients and a first set of time points when the notifications were received by the first subset of recipients stored in one or more database systems;
identifying, from the set of recipients, a second subset of recipients that (i) have received the notification through the second channel, (ii) have not received the notification through the first channel, and (iii) have received the treatment, wherein the identifying is based on (i) the de-identified medical records indicating treatments received by the set of anonymized patients and (ii) the notification records indicating channels through which notifications were provided to the second subset of recipients and a second set of time points when the notifications were received by the second subset of recipients stored in the one or more database systems;
generating a multi-channel impact model based on a time relationship between when the treatment was received by each patient of the set of anonymized patients and when a notification was received by each recipient of the first subset of recipients and the second subset of recipients, wherein the multi-channel impact model represents an impact of notifications being provided through the first channel and the second channel on a likelihood of one or more recipients in the set of recipients receiving the treatment;
generating a notification plan for timely notifying potential patients of treatments based on the impact represented by the multi-channel impact model, wherein the notification plan indicates one or more notifications to be provided through a corresponding channel to increase a number of treatments to be subsequently received; and
sending the one or more notifications through the first channel or the second channel to respective recipients associated with potential patients based on the notification plan.

9. The system of claim 8, wherein the first channel comprises a digital channel and the second channel comprises a non-digital channel.

10. The system of claim 8, wherein the operations comprise:
generating a first channel impact model based on the first subset of recipients, wherein the first channel impact model represents a first impact of the notification received through the first channel and treatments received by the first subset of recipients; and
generating a second channel impact model based on the second subset of recipients, wherein the second channel impact model represents a second impact of the notification received through the second channel and treatments received by the second subset of recipients.

11. The system of claim 10, wherein the multi-channel impact model is generated based on the first impact represented by the first channel impact model and the second impact represented by the second channel impact model.

12. The system of claim 10, wherein generating the first channel impact model comprises:
determining a time decay factor associated with the first impact represented by the first channel impact model; and
determining, based on the time decay factor, an expected time delay before the notification received through the first channel is expected to impact whether treatments are received by the first subset of recipients.

13. The system of claim 8, wherein each recipient included in the first subset of recipients and the second subset of recipients is associated with a unique identifier that distinguishes a recipient from other recipients.

14. The system of claim 8, wherein the multi-channel impact model is generated based on:
oversampling data associated with the first subset of recipients and the second subset of recipients; and
undersampling data associated with other recipients not included in either the first subset of recipients and the second subset of recipients.

15. At least one non-transitory computer-readable storage device storing instructions that cause one or more processors to perform operations comprising:
identifying, from a set of recipients, a first subset of recipients that (i) received a notification through a first channel, (ii) have not received the notification through a second channel, and (iii) have received a treatment, wherein the identifying is based on (i) de-identified medical records indicating treatments received by a set of anonymized patients and (ii) notification records indicating channels through which notifications were provided to the first subset of recipients and a first set of time points when the notifications were received by the first subset of recipients stored in one or more database systems;
identifying, from the set of recipients, a second subset of recipients that (i) have received the notification through the second channel, (ii) have not received the notification through the first channel, and (iii) have received the treatment, wherein the identifying is based on (i) the de-identified medical records indicating treatments received by the set of anonymized patients and (ii) the notification records indicating channels through which notifications were provided to the second subset of recipients and a second set of time points when the notifications were received by the second subset of recipients stored in the one or more database systems;
generating a multi-channel impact model based on a time relationship between when the treatment was received by each patient of the set of anonymized patients and when a notification was received by each recipient of the first subset of recipients and the second subset of recipients, wherein the multi-channel impact model represents an impact of notifications being provided through the first channel and the second channel on a likelihood of one or more recipients in the set of recipients receiving the treatment;

generating a notification plan for timely notifying potential patients of treatments based on the impact represented by the multi-channel impact model, wherein the notification plan indicates one or more notifications to be provided through a corresponding channel to increase a number of treatments to be subsequently received; and sending the one or more notifications through the first channel or the second channel to respective recipients associated with potential patients based on the notification plan.

16. The at least one non-transitory computer-readable storage device of claim 15, wherein the first channel comprises a digital channel and the second channel comprises a non-digital channel.

17. The at least one non-transitory computer-readable storage device of claim 15, wherein the operations further comprise:

generating a first channel impact model based on the first subset of recipients, wherein the first channel impact model represents a first impact of the notification received through the first channel and treatments received by the first subset of recipients; and generating a second channel impact model based on the second subset of recipients, wherein the second channel impact model represents a second impact of the notification received through the second channel and treatments received by the second subset of recipients.

18. The at least one non-transitory computer-readable storage device of claim 17, wherein the multi-channel impact model is generated based on the first impact represented by the first channel impact model and the second impact represented by the second channel impact model.

19. The at least one non-transitory computer-readable storage device of claim 17, wherein generating the first channel impact model comprises:

determining a time decay factor associated with the first impact represented by the first channel impact model; and determining, based on the time decay factor, an expected time delay before the notification received through the first channel is expected to impact whether treatments are received by the first subset of recipients.

20. The at least one non-transitory computer-readable storage device of claim 15, wherein each recipient included in the first subset of recipients and the second subset of recipients is associated with a unique identifier that distinguishes a recipient from other recipients.

* * * * *